United States Patent [19]

Lecolier et al.

[11] 4,297,301

[45] Oct. 27, 1981

[54] PROCESS FOR THE MANUFACTURE OF ORGANIC ACID CHLORIDES

[75] Inventors: Serge L. Lecolier, Janville sur Juine; Jean-Pierre G. Senet, La Chapelle la Reine, both of France

[73] Assignee: Societe Nationale des Poudres et Explosifs, Paris, France

[21] Appl. No.: 96,657

[22] Filed: Nov. 23, 1979

[30] Foreign Application Priority Data

Nov. 29, 1978 [FR] France .............................. 78 33670
Aug. 30, 1979 [FR] France .............................. 79 21730

[51] Int. Cl.³ .......................................... C07C 51/60
[52] U.S. Cl. .................................. 260/544 K; 260/408
[58] Field of Search ........................... 260/544 K, 408

[56] References Cited

U.S. PATENT DOCUMENTS 3,857,841 12/1974 Keil .................................. 260/250

OTHER PUBLICATIONS

Babad et al., Chem. Reviews 73, 82(1973).

Primary Examiner—Robert Gerstl
Attorney, Agent, or Firm—Bucknam and Archer

[57] ABSTRACT

The invention relates to a process for the manufacture of carboxylic acid chlorides by the phosgenation, under the action of heat, of the corresponding acids in the presence of a catalyst.

The process according to the invention is characterized in that a compound possessing the skeleton

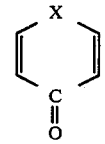

is used as the catalyst, in which compound X is an oxygen atom or a nitrogen atom substituted by an alkyl group.

15 Claims, No Drawings

PROCESS FOR THE MANUFACTURE OF ORGANIC ACID CHLORIDES

The present invention relates to a process for the manufacture of organic acid chlorides by the phosgenation of the corresponding organic acids or organic acid anhydrides in the presence of a catalyst.

It is known to use a catalyst to permit the production of acid chlorides by reacting phosgene with the corresponding acids or anhydrides at a moderate temperature and at a pressure similar to atmospheric pressure.

Thus, French Pat. Nos. 732,078 and 2,212,319 proposed the use of tertiary amines. However, since these latter catalysts have a very mediocre activity, consequently requiring the use of a high temperature and giving rise in certain cases to the formation of troublesome by-products, other solutions to the problem were proposed.

Thus, it was proposed to employ amides, ureas, thioureas or pyrrolidones, such as dimethylformamide, tetramethylurea, tetramethylthiourea and N-alkylpyrrolidones, as described, in particular, in German Pat. No. 1,026,750, U.S. Pat. Nos. 3,318,950 and 3,544,627 and French Patent 2,196,305. Although these substances bring about considerable progress from the point of view of the catalytic activity, there is the disadvantage that they lead, after a few recycling operations, to the formation of sludges which block the pipelines, and also, in general, to the formation of secondary by-products which are sometimes toxic and frequently difficult to separate from the acid chloride.

At the same time, inorganic catalysts, such as active charcoal, and Lewis bases have the advantage that they give rise to only a small amount of by-products, if any; on the other hand, however, they possess a reduced catalytic activity, requiring the use of high reaction temperatures. Such catalysts are described in U.S. Pat. Nos. 2,156,177 and 2,272,299 and do not represent a satisfactory solution to the problem because of the technological difficulties (filtration and distillation) caused by the presence of solids in the reactor.

Two solutions which are almost satisfactory have recently been proposed firstly in U.S. Pat. Nos. 3,547,960 and 3,869,485 and secondly in U.S. Pat. No. 3,962,326. According to U.S. Pat. No. 3,547,960, a member of the imidazole family is used. This gives a rapid reaction without the formation of by-products. Unfortunately, in certain cases, it is found that two phases are formed in the reactor and this becomes troublesome after a few recycling operations. According to U.S. Pat. No. 3,962,326, a tertiary phosphine oxide or sulphide is employed. In this case, the catalytic action is good, even with low proportions of catalysts, and only a small amount of by-products is formed, if any, provided that the catalyst is not recycled. In fact, in this latter case, the tertiary phosphine dichloride, which is responsible for the chlorination and which is formed by the reaction of phosgene with the phosphine oxide, according to German Pat. No. 1,192,215, partially decomposes when the acid chloride formed is distilled. It follows that the batch of catalyst cannot satisfactorily be recycled.

Therefore, it is seen that it still remains to discover catalysts which, at one and the same time, have a good activity at a moderate temperature and are well suited to recycling operations, and which do not lead to the formation of a troublesome proportion of by-products.

Applicants have now discovered a family of catalysts which corresponds to the abovementioned properties and which is consequently of very great industrial value.

The invention relates to a process for the manufacture of organic acid chlorides by the phosgenation, under the action of heat, of the corresponding acids or acid anhydrides in the presence of a catalyst, characterised in that at least one member of the family of the general formula (I)

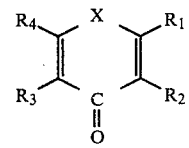

is used as the catalyst, in which formula X is an oxygen atom or a nitrogen atom which is monosubstituted by a group $R_5$, which is an alkyl group containing from 1 to 6 carbon atoms, and in which formula $R_1$, $R_2$, $R_3$ and $R_4$ are all different, or at least two of them are the same, and are a hydrogen atom or an organic radical which may or may not be capable of reacting with phosgene. Preferably, when the radicals $R_1$, $R_2$, $R_3$ and/or $R_4$ are organic radicals, they do not contain more than 20 carbon atoms.

Throughout the following text, the term catalysts denotes members of the family of the general formula (I).

Amongst the catalysts to which the process according to the present invention relate, some are preferred for their high catalytic activity. Thus, catalysts which are particularly preferred are those of the general formula (I) in which, on the one hand, $X=O$ or $N-R_5$, $R_5$ being a linear or branched $C_1$ to $C_6$ alkyl group, and, on the other hand, $R_1=H$, a linear or branched $C_1$ to $C_{12}$ alkyl group which may or may not be substituted by chlorine atoms, hydroxyl groups, carboxyl groups, ester groups or ether groups, an aryl group which may or may not be substituted by one or more halogen, hydroxyl or carboxyl groups, a $C_7$ to $C_{20}$ aralkyl group, a $C_7$ to $C_{20}$ alkaryl group, a hydroxyl group, a carboxyl group, or a $C_1$ to $C_3$ dialkylamino group, $R_2$ and $R_3$ are identical or different and have one of the possible meanings for $R_1$, and optionally the same meaning as $R_1$, or, if $X=N-R_5$, they are both preferably a hydrogen atom, and $R_4$ has one of the possible meanings for $R_1$, and optionally has the same meaning as $R_1$ and/or as $R_2$ and/or $R_3$, or alternatively $R_1$ and $R_2$ taken together, and/or $R_3$ and $R_4$ taken together, form a phenyl group.

According to a particularly preferred embodiment of the invention, the compounds used as the catalyst are those of the general formula (I) in which, on the one hand, $X=O$ or $N-R_5$, $R_5$ being a linear or branched $C_1$ to $C_6$ alkyl group, and, on the other hand:

$R_1=R_2=R_3=R_4=H$, or alternatively:

$R_1=R_4=C_1$ to $C_6$ alkyl and $R_2=R_3=H$, or alternatively in which $X=O$ and:

$R_1=R_4=H$ and $R_2$ and $R_3=C_1$ to $C_6$ alkyl, $R_1=R_4=H$ and $R_2$ and $R_3=$aryl which may or may not be substituted by halogen, hydroxyl or carboxyl groups, $R_1=R_4=H$ and $R_2$ and $R_3=C_7$ to $C_{20}$ aralkyl or $C_7$ to $C_{20}$ alkaryl, or $R_1=R_4=COOH$ and $R_2$ and $R_3=H$ or $C_1$ to $C_6$ alkyl.

In general terms, compounds which are to be considered as falling within the scope of the invention are any compounds which are substituted by groups which are unreactive towards phosgene, or any compounds which are substituted by groups which are reactive towards phosgene, but, after reacting with phosgene, are converted into a stable molecule in which the main skeleton:

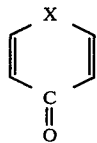

is preserved.

Surprisingly, it has been found that, although all the abovementioned compounds are active as a catalyst for the phosgenation of acids, some of them have a much more pronounced activity than others from the point of view of accelerating the reaction rate.

Thus, in general terms, it has been found that the catalysts according to the invention are particularly powerful both with regard to the reaction of phosgene with the acid and with regard to the reaction of phosgene with the corresponding anhydride, whether the latter be the starting reactant or whether it be formed in situ, during phosgenation, by the reaction of the acid chloride already formed with the starting acid. Furthermore, it has been found that a catalyst according to the invention is in general the more active, the less bulky are the substituents $R_2$ and $R_3$ which it contains, such as H, the nature of the substituents $R_1$ and $R_4$ being less important, although the groups $R_1$ and $R_4$ should preferably also be of low bulk.

As has been stated, it is perfectly possible to use catalysts, according to the invention, which are reactive towards phosgene by virtue of the substituents which they carry. However, their use is not preferred because it leads to an unnecessary additional consumption of phosgene and to the production of a molecule which, although efficient, has an efficiency which, on average, is less than that of the starting catalysts.

The carboxylic acids to which the present process applies are, in particular, aliphatic carboxylic acids having 2 to 20 carbon atoms and aromatic or cycloaliphatic acids containing from 4 to 24 carbon atoms. The above acids in question are those containing from 1 to 3 carboxyl groups. The present invention also relates to the anhydrides of the above acids. Examples which may be mentioned are the following typical acids: acetic acid, butyric acid, 2-ethylhexanoic acid, 3,5,5-trimethylhexanoic acid, lauric acid, palmitic acid, stearic acid, cyclohexanecarboxylic acid, cyclohexane-1,4-dicarboxylic acid, benzoic acid, chlorobenzoic acids, nitrobenzoic acids, chloronitrobenzoic acids, phthalic acid, terephthalic acid, isophthalic acid, trimellitic acid, cyclohexanedicarboxylic acid and $\alpha,\beta$-unsaturated carboxylic acids. The phosgenation of $\alpha,\beta$-unsaturated carboxylic acids, such as acrylic acid, gives $\alpha,\beta$-unsaturated carboxylic acid chlorides, or, as a result of the addition of hydrogen chloride, $\beta$-chlorocarboxylic acid chlorides.

According to the present invention, amounts of catalyst from 0.01 to 10%, preferably from 0.1 to 2%, by weight, relative to the carboxylic acid or its anhydride, are used in order to bring the reaction to completion in an advantageously short period of time. It has been observed that the overall reaction rate increases with the proportion of catalyst used in the medium.

The range of temperatures used for preparing the acid chlorides in accordance with the process according to the invention largely depends on the starting acid or anhydride. A temperature of between 70° and 180° C., and preferably between 90° C. and 150° C., is advantageously used. As a general rule, a temperature above the melting point of the starting acid or anhydride is preferably used. However, it is equally possible to carry out the reaction on acids or anhydrides which are suspended or dissolved in a solvent or an organic suspending agent which is inert towards phosgene, such as an aromatic solvent. An acid chloride, in particular the same acid chloride which it is desired to prepared, originating from a previous production, can also be used as the solvent.

The process according to the invention operates either discontinuously or continuously and its application does not involve modifying the equipment known by those skilled in the art. The process can operate using a pressure above atmospheric pressure, but the quality of the catalysts according to the invention is such that it is not generally necessary to resort to this expedient.

The reaction time can vary according to the nature of the acid or anhydride treated and according to the degree of completion and the purity which it is desired to achieve. In the present process, a duration of 2 to 10 hours is sufficient to obtain acid chlorides having the usual purity required for their applications, with an excellent yield.

As regards the relative proportions of reactants to be employed in accordance with the present process, they do not differ from those employed in the conventional processes, that is to say a molar ratio phosgene/acid or anhydride group present in the molecule of about 1 is used, a slight excess of phosgene being desirable in order to compensate the losses due to entrainment by gases (HCl and $CO_2$).

It is therefore seen that the catalysts used within the scope of the process according to the invention have a catalytic activity which is comparable to that of the best catalysts known. However, the catalysts according to the invention have the additional advantage, which is very important industrially, that they possess excellent heat stability, which permits several recycling operations without a substantial loss of catalytic activity, and which also makes it possible to separate off and purify the acid chlorides by distilling the crude reaction mixture, without necessitating careful control of the temperature. The use of these catalysts therefore results in reduced manufacturing costs and improved productivity.

The catalysts according to the present invention are well-known compounds, the synthesis of which has been described in the publicly available literature. For example, in the case of compounds in which $X=N—R_5$, there may be mentioned the synthesis reported in the article by A. F. EL KASCHEF and M. H. NOSSEIR in the Journal of the American Chemical Society (1960), 82, pages 4,344–47, which consists in reacting a primary amine of the formula $R_5NH_2$ with a $\gamma$-pyrone of the formula

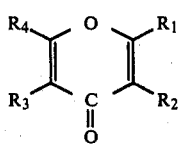

These pyrones can themselves be synthesised by the method described by WILLSTATTER AND PUMMERER, Berichte, 37, pages 3,734 to 3,744 (1905), who recommend the decarboxylation of chelidonic acid, which is itself obtained, according to Organic Synthesis, Volume 2, pages 41 et seq., by dehydrating the product resulting from the reaction of acetone with ethyl oxalate.

The following illustrative embodiments of the process according to the invention are given by way of simple non-limiting illustrations of the invention.

EXAMPLE 1

Synthesis of 2-ethylhexanoyl chloride

One mol of 2-ethylhexanoic acid and 10 millimols of N-methyl-4-pyridone were introduced into a 250 ml reactor equipped with a mechanical stirrer, a thermometer, a dip tube and a reflux condenser cooled to $-70°$ C. The mixture was then heated to $115°-120°$ C.

Phosgene gas was added at this temperature at the rate of 120 g in the course of two hours, the flow of phosgene being adjusted so that gentle reflux in the condenser was observed.

When the addition of the phosgene was complete, stirring was continued for 1 and a half hours, still at $115°-120°$ C.

After degassing with nitrogen, the 2-ethylhexanoyl chloride obtained was distilled under reduced pressure.

The product is of satisfactory purity. After distillation, the yield is 80%, relative to the acid.

EXAMPLE 2

The same procedure as above was followed, but only 1 mmol of the same catalyst was used. 110 g of phosgene were introduced in the course of 1 hour 55 minutes. The yield obtained is 87%, after distillation.

EXAMPLE 3

The amount of catalyst used was again reduced. 0.1 mmol of N-methyl-4-pyridone was used and 112 g of phosgene were introduced in the course of 4 hours 45 minutes, the other conditions described in the previous examples being observed.

A yield of 89% was obtained, after distillation.

EXAMPLE 4

Still adopting the procedure of Example 1, 10 mmols of N-butyl-4-pyridone were used and 118 g of phosgene were introduced in the course of 3 hours.

The yield of 2-ethylhexanoyl chloride was 86%, after distillation.

EXAMPLE 5

This time, 10 mmols of N-methyl-2,6-dimethyl-4-pyridone were used and 117 g of phosgene were introduced in the course of 2 and a half hours. A yield of 89% of 2-ethylhexanoyl chloride was obtained, after distillation.

EXAMPLE 6

122 g of benzoic acid, 140.5 g of xylene and 0.96 g (0.01 mol) of 4H-pyran-4-one were placed in a 500 ml reactor equipped with a stirrer, a thermometer, a gas inlet tube and a reflux condenser at $-40°$ C.

The reaction medium was heated to $120°-125°$ C., whilst stirring, and phosgene gas was introduced as rapidly as possible without causing any substantial reflux in the condenser.

Thus, 112 g of phosgene are introduced in the course of 2 hours 30 minutes. When the introduction of the phosgene is complete, the temperature is kept at $120°$ C. for a further 1 hour, after which the mixture is degassed with nitrogen in order to complete the removal of hydrogen chloride, carbon dioxide and excess phosgene.

A very pure product (97% pure according to the proportion of hydrolysable chlorine) is thus obtained, which can be purified by distillation if desired. The yield is virtually 100%.

EXAMPLE 7

By way of comparison with the preceding example, the operation was repeated under the same conditions, but the 0.01 mol of 4H-γ-pyrone was replaced by 0.01 mol (2.84 g) of tetrabutylurea. Tetrabutylurea is a catalyst of the carbonamide type which gives rise to a fairly small amount of by-products, and the latter can readily be separated off.

It is then found that 3 hours 30 minutes are required in order to introduce all the necessary phosgene (114 g), which brings the total time required to achieve the purity reported in Example 1 to 4 hours 30 minutes.

EXAMPLE 8

The reaction was carried out with the same apparatus as in Example 6 and 113 g (0.5 mol) of benzoic anhydride, 150.5 g of xylene and 0.01 mol (0.96 g) of 4H-γ-pyrone were placed in the reactor. The medium obtained was heated to $100°-115°$ C., whilst stirring, and phosgene was introduced as indicated in Example 1.

The following table reports the amounts of phosgene introduced and the degree of completion of the reaction (determined by measuring the proportion of hydrolysable chlorine after carefully degassing the sample) as a function of time.

| Time (minutes) | Phosgene introduced g | mols | Degree of completion (%) |
|---|---|---|---|
| 40 | 24.7 | 0.25 | 31 |
| 66 | 48.8 | 0.49 | |
| 80 | 56.2 | 0.57 | 91 |

It is found that 4H-γ-pyrone permits rapid phosgenation of benzoic anhydride, which is at least as rapid as in the case of benzoic acid.

EXAMPLE 9

If the reaction is carried out strictly as in Example 8, the 4H-γ-pyrone being replaced by tetrabutylurea (0.01 mol or 2.84 g), the following table is obtained:

| Time (minutes) | Phosgene introduced g | mols | Degree of completion (%) |
|---|---|---|---|
| 40 | 24.6 | 0.25 | 28 |
| 60 | 47.4 | 0.48 | |

-continued

| Time (minutes) | Phosgene introduced | | Degree of completion (%) |
|---|---|---|---|
| | g | mols | |
| 80 | 54.2 | 0.55 | 60 |

It is therefore found that 4H-γ-pyrone permits much more rapid phosgenation than tetrabutylurea.

EXAMPLE 10

0.01 mol (2.36 g) of 2,6-dipropyl-3,5-diethylpyran-4-one was used and this was placed in a 250 ml reactor, equipped as in Example 6, together with 144 g (1 mol) of 2-ethylhexanoic acid.

The mixture was heated to 100°–115° C., whilst stirring, and 118 g of phosgene gas were introduced in the course of 4 hours 15 minutes so as to cause very gentle reflux in the condenser.

The mixture is stirred for a further 1 hour at 110° C., after which the excess phosgene is removed, by degassing with nitrogen, to give 157 g of crude acid chloride, that is to say a yield of 97%.

After distillation under reduced pressure (104°–106° C./90 mm Hg), carried out in an apparatus equipped with a simple Vigreux column, 146.3 g of 2-ethylhexanoyl chloride are collected (yield 90%), which is more than 99% pure. 7 g of residue remain in the still. The same experiment is repeated, using the abovementioned residue of 7 g as the catalyst. 162.7 g of crude acid chloride are thus obtained, which, after distillation, yield 129.2 g of a product which is more than 99% pure, with a distillation residue of 27 g.

After a further two recycling operations, the mass of residue remained constant at about 45 g.

EXAMPLE 11

Synthesis of benzoyl chloride

The procedure described in Example 1 was used and was applied to a solution of 1 mol of benzoic acid in 140 g of xylene. The reaction was carried out in the presence of 10 mmols of N-butyl-4-pyridone. 120 g of phosgene were introduced in the course of 2 hours 40 minutes. The yield obtained after distillation is 98.5%. Infra-red spectrometry did not reveal any trace of benzoic anhydride in the residue. The latter was recycled and a further batch of one mol of benzoic acid was introduced into the reactor. 120 g of phosgene are introduced in the course of 3 hours and the usual cycle is followed. A yield of 96% of benzoyl chloride was obtained after distillation. The residue still showed no traces of anhydride in infra-red spectrometry.

EXAMPLE 12

The procedure of Example 6 was followed, using 122 g of benzoic acid, 140.5 g of xylene and 0.01 mol (2.36 g) of 2,6-dipropyl-3,5-diethylpyran-4-one.

The mixture is heated to 120° C., whilst stirring, and phosgene is introduced as rapidly as possible without, however, causing substantial reflux in the condenser. After the introduction of the phosgene is complete, the reaction mixture is kept at 120° C. for one hour, after which the excess phosgene is removed by degassing with nitrogen.

The benzoyl chloride obtained was separated off by distillation using a Vigreux column having a separating capacity of the order of one theoretical plate. The xylene thus leaves at the top of the column, entraining part of the acid chloride. The following table thus indicates only the yield of distilled acid chloride which is more than 99.5% pure.

In order to demonstrate the possibility of recycling the catalyst several times without loss of catalytic activity, four successive recycling operations were carried out on the above distillation residue, all other conditions being the same. The results obtained are reported in the table below.

| Recycling operation no. | Phosgenation time | Amount of phosgene introduced | Yield (1) | Residue (catalyst + anhydride) |
|---|---|---|---|---|
| 0 | 3 hours | 111 g | 70% | 27 g |
| 1 | 3 hours | 105 g | 71.4% | 34.5 g |
| 2 | 3 hours 30 minutes | 106 g | 75.5% | 46.2 g |
| 3 | 2 hours 30 minutes | 117 g | 73.3% | 46.6 g |
| 4 | 3 hours | 110 g | 74% | 46.4 g |

(1) of distilled product (>99.5% pure).

It is found that there is no loss of catalytic activity, since the phosgenation time is essentially constant, and that the proportion of anhydride remains constant, as from the second recycling operation, at a value which is peculiar to the catalyst and depends on the rate constants for the phosgenation of the acid and its anhydride.

EXAMPLE 13

0.96 g (0.01 mol) of 4H-pyran-4-one and 88 g (1 mol) of n-butyric acid are used and these are placed in a 250 ml reactor equipped as in Example 6.

The mixture is heated to 100°–115° C., whilst stirring, and phosgene is introduced in the course of about 4 hours so as to cause gentle reflux in the condenser. After the introduction of the phosgene is complete, the reaction mixture is kept at 95° C. for 1 hour and the excess phosgene is then removed by degassing with anhydrous nitrogen.

The butyryl chloride obtained is separated off by distillation using a Vigreux column.

In order to demonstrate, in this case also, the possibility of recycling the catalyst several times without substantial loss of catalytic activity, 2 successive recycling operations were carried out on the above distillation residue, all other conditions being the same.

The results obtained are recorded in the table below, which also indicates the result of an experiment carried out under the same conditions but without a catalyst.

| Experiment | Catalyst | Amount of phosgene introduced | Yield (1) | Amount of residue |
|---|---|---|---|---|
| comparison | none | 100 g | 0 | — |
| 1 | 4H-pyran-4-one 0.01 mol | 108 g | 75% | 11.1 g |
| 2 | residue from experiment 1 | 108 g | 76% | 5.2 g |
| 3 | residue from experiment 2 | 108 g | 75% | 11 g |

(1) of distilled product (>99% pure)

EXAMPLE 14

4 kg, that is to say 38 mols, of 2-ethylhexanoic acid and 34.5 g, that is to say 0.277 mol, of 2,6-dimethyl-γ- pyranone were used and these were placed in a 10 liter reactor.

The mixture was heated to 90° C. and phosgene was passed through so as to cause gentle reflux in the reactor condensers; 4 kg, that is to say 40.6 mols, of phosgene were thus introduced in the course of 2 hours 45 minutes. After stirring for one hour, the contents of the reactor were degassed by passing nitrogen through so as to drive off the hydrogen chloride, the carbon dioxide and the excess phosgene; by distillation under reduced pressure, 4.330 kg of 98% pure acid chloride are obtained, that is to say a yield of 96%.

EXAMPLE 15

3.905 kg (36.9 mols) of 2-ethylhexanoic acid and 26 g (0.26 mol) of 4H-γ-pyranone are introduced into a 10 liter reactor.

The mixture is heated to 130° C., whilst stirring, and phosgene gas is introduced at the rate of 8.33 mols/hour so as to maintain very gentle reflux in the reactor condenser.

3.300 kg of phosgene are thus introduced in the course of 4 hours. The mixture is stirred for 1 hour at 130° C., after which the product obtained is degassed with nitrogen in order to remove the hydrogen chloride, the carbon dioxide and the excess phosgene.

The 2-ethylhexanoic acid chloride, boiling point (10 mm Hg)=62° C., is distilled in vacuo; 4.285 kg of 99% pure acid chloride, that is to say a yield of 97.4% and 130 g of distillation residues, consisting of the catalyst batch and a small amount of residual acid chloride, are thus obtained.

These distillation residues are recycled with a batch of 3.905 kg of fresh 2-ethylhexanoic acid, heated to 130° C. and phosgenated under the above conditions, the flow of phosgene making it possible to achieve very gentle reflux in the condenser being 9.4 mols/hour; after a phosgenation time of 3 hours 40 minutes, significant reflux in the condenser is achieved, indicating the end of the reaction. The mixture is allowed to react for 3 hours, degassed and then distilled under the above conditions, and 3.9 g of acid chloride and 0.7 g of residues, which are recycled in a subsequent operation, are obtained.

The following table gives the reaction times, amounts of distillation residues and yield of acid chloride obtained in a series of recycling operations.

| Operation | Total reaction time | Amount of distillation residues recycled | Yield of acid chloride |
|---|---|---|---|
| 1 | 4 hours | 0.130 kg | 97.4% |
| 2 (1st recycling) | 7 hours | 0.700 kg | 85% |
| 3 (2nd recycling) | 7 hours | 0.700 kg | 83.4% |
| 4 (3rd recycling) | 7 hours | 0.700 kg | 88.9% |

EXAMPLE 16

Synthesis of acryloyl chloride

The same procedure as in Example 1 was used and this was applied to 1 mol of acrylic acid in the presence of 10 mmols of N-butyl-4-pyridone.

113 g of phosgene were introduced in the course of 3 hours 10 minutes.

Acryloyl chloride was obtained with a yield of 64%, after distillation.

We claim:

1. Process for the manufacture of a carboxylic acid chloride which consists of phosgenating at a temperature of 90°–150° C., the corresponding acid or acid anhydride in the presence of a catalyst, wherein the catalyst is at least one member selected from the grop consisting of compounds of formula (I)

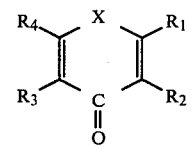

in which X is oxygen or nitrogen which is monosubstituted by $R_5$, which is an alkyl containing from 1 to 6 carbon atoms, and in which formula $R_1$, $R_2$, $R_3$ and $R_4$ are all different, or at least two of them are the same, and are hydrogen or an organic radical which contains at most 20 carbon atoms and wherein the proportion of the catalyst relative to said acid or anhydride, is between 0.01 and 10% by weight.

2. Process of manufacture according to claim 1, wherein the catalyst is a member selected from the group consisting of compounds of formula:

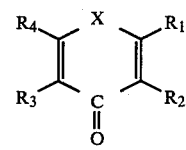

in which, X=O or N—$R_5$, $R_5$ being a linear or branched $C_1$ to $C_6$ alkyl, and, $R_1=R_2=R_3=R_4=H$, or alternatively:

$R_1=R_4=C_1$ to $C_6$ alkyl and $R_2=R_3=H$, alternatively X=O and:

$R_1=R_4=C_1$ to $C_6$ alkyl and $R_2$ and $R_3=C_1$ to $C_6$ alkyl, $R_1=R_4=H$ and $R_2$ and $R_3=$aryl wherein the aryl is unsubstituted or substituted by halogen, hydroxyl or carboxyl, $R_1=R_4=H$ and $R_2$ and $R_3=C_7$ to $C_{20}$ aralkyl or $C_7$ to $C_{20}$ alkaryl, or $R_1=R_4=COOH$ and $R_2$ and $R_3=H$ or $C_1$ to $C_6$ alkyl.

3. Process of manufacture according to claim 2, wherein the catalyst is 4H-pyran-4-one.

4. Process of manufacture according to claim 2, wherein the catalyst is N-butyl-4-pyridone.

5. Process according to claim 1, wherein the reaction is carried out using, as the solvent, the acid chloride which it is desired to prepare.

6. Process of manufacture according to claim 1 wherein the catalyst is a member selected from the group consisting of compounds of formula

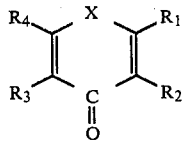

in which, X=O or N—$R_5$, $R_5$ being a linear or branched $C_1$ to $C_6$ alkyl, $R_1$, $R_2$, $R_3$ and $R_4$ are H, a linear or branched $C_1$ to $C_{12}$ unsubstituted alkyl or alkyl substituted by chlorine, hydroxyl, carboxyl, ester groups of ether groups, an unsubstituted aryl or aryl substituted by at least one halogen, hydroxyl or carboxyl, $C_7$ to $C_{20}$ aralkyl, $C_7$ to $C_{20}$ alkaryl, hydroxyl, carboxyl, or $C_1$ to $C_3$ dialkylamino or $R_1$ and $R_2$ taken together form a phenyl or $R_3$ and $R_4$ taken together form a phenyl or $R_1$ and $R_2$ taken together and $R_3$ and $R_4$ taken together form a phenyl.

7. The process according to claim 6 wherein X=$NR_5$ and $R_2$ and $R_3$ are both hydrogen.

8. The process according to claim 6 wherein at least one of $R_2$, $R_3$ and $R_4$ is the same as $R_1$.

9. The process according to claim 6, 7 or 8 wherein at least two of $R_2$, $R_3$ and $R_4$ are the same.

10. The process according to claim 1 wherein the catalyst is recycled.

11. The process according to claim 1 wherein the catalyst is inert to phosgene.

12. The process according to claim 1 wherein the catalyst reacts with phosgene to give a stable compound still having the skeleton

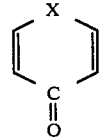

13. The process according to claim 1 wherein said carboxylic acid or anhydride is a di- or tri-carboxylic acid or anhydride.

14. The process according to claim 1 wherein said carboxylic acid or anhydride is α,β-unsaturated and the carboxylic acid chloride contains chlorine in the β-position.

15. The process according to claim 1 wherein said catalyst is in an amount of 0.1–2% by weight relative to said carboxylic acid or said anhydride.

* * * * *